United States Patent [19]
Grace

[11] Patent Number: 6,132,441
[45] Date of Patent: Oct. 17, 2000

[54] RIGIDLY-LINKED ARTICULATING WRIST WITH DECOUPLED MOTION TRANSMISSION

[75] Inventor: Kenneth Grace, Carpinteria, Calif.

[73] Assignee: Computer Motion, Inc., Goleta, Calif.

[21] Appl. No.: 09/287,860

[22] Filed: Apr. 7, 1999

Related U.S. Application Data

[63] Continuation-in-part of application No. 09/262,134, Mar. 3, 1999, which is a continuation-in-part of application No. 08/873,190, Jun. 11, 1997, Pat. No. 6,102,850, which is a continuation-in-part of application No. 08/755,063, Nov. 22, 1996, Pat. No. 5,855,583.

[51] Int. Cl.[7] ............................. A61B 19/00; B25J 11/00
[52] U.S. Cl. ............................. 606/147; 606/208; 901/8
[58] Field of Search ................ 606/147, 205, 606/208; 395/80, 86; 318/568.11; 901/8

[56] References Cited

U.S. PATENT DOCUMENTS

| | | |
|---|---|---|
| 4,491,135 | 1/1985 | Klein ................................ 606/147 |
| 4,949,717 | 8/1990 | Shaw ................................ 606/147 |
| 5,201,743 | 4/1993 | Harber et al. ..................... 606/147 |
| 5,257,999 | 11/1993 | Slanetz, Jr. ....................... 606/147 |
| 5,304,185 | 4/1994 | Taylor .............................. 606/147 |
| 5,417,701 | 5/1995 | Holmes ............................ 606/148 |
| 5,792,178 | 8/1998 | Welch et al. ..................... 606/208 |
| 5,860,995 | 1/1999 | Berkelaar ......................... 606/208 |
| 5,904,702 | 5/1999 | Ek et al. .......................... 606/206 |
| 5,906,630 | 5/1999 | Anderhub et al. ................ 606/205 |
| 5,951,587 | 9/1999 | Qureshi et al. ................... 606/207 |
| 5,954,731 | 9/1999 | Yoon ................................ 606/144 |
| 5,984,932 | 11/1999 | Yoon ................................ 606/147 |

*Primary Examiner*—Gary Jackson
*Attorney, Agent, or Firm*—Irell & Manellla LLP

[57] ABSTRACT

The present invention is a device having a rigidly linked jaw that is decoupled from an articulating wrist. The device provides for articulating motion as well as actuation that may be used in grasping, cutting, suturing or the like.

1 Claim, 3 Drawing Sheets

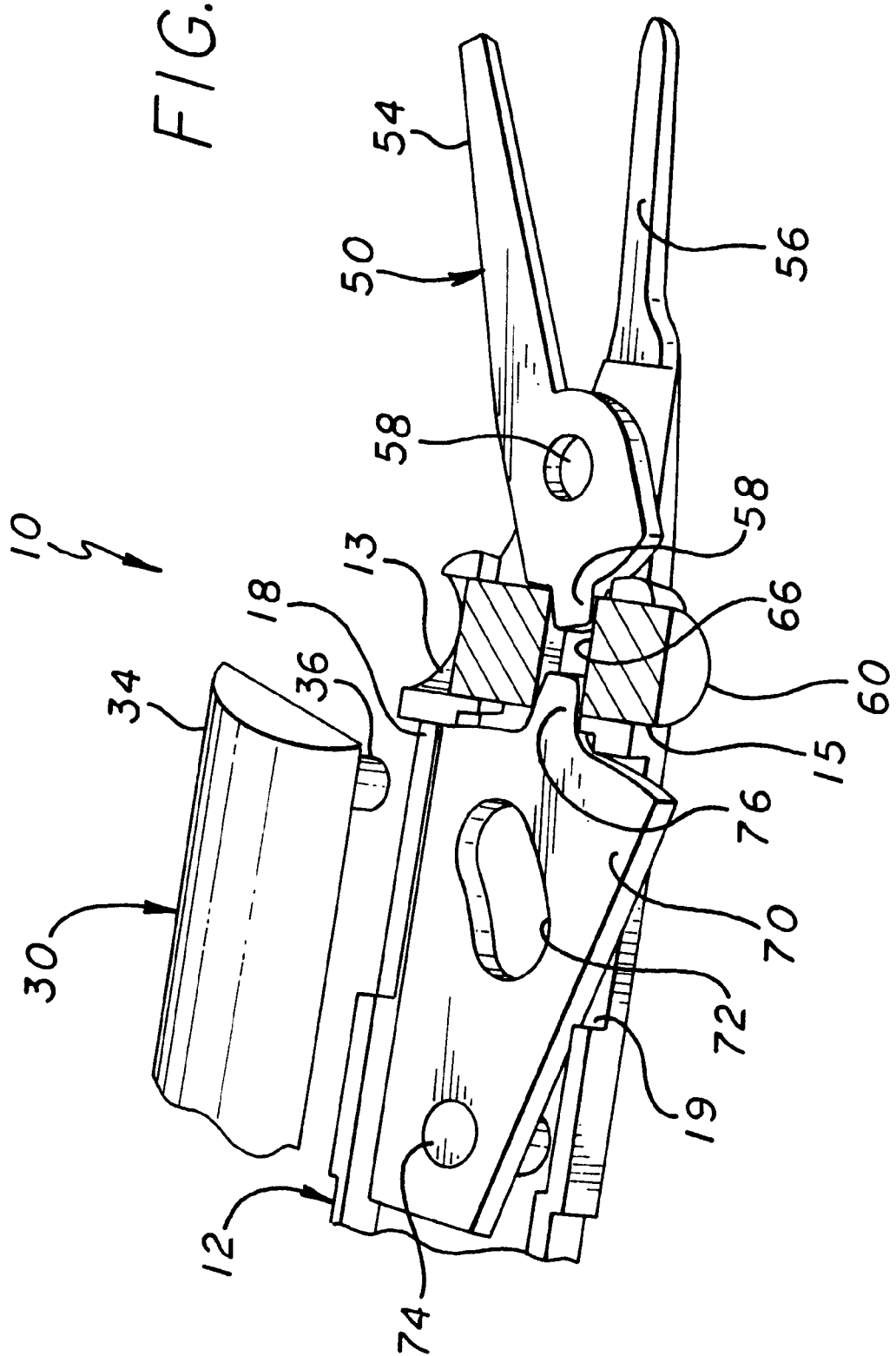

RIGIDLY-LINKED ARTICULATING WRIST WITH DECOUPLED MOTION TRANSMISSION

CROSS-REFERENCE TO RELATED APPLICATIONS

This application is a continuation-in-part of application Ser. No. 09/262,134, filed Mar. 3, 1999, pending, which is a continuation-in-part of application Ser. No. 08/873,190, filed Jun. 11, 1997, now U.S. Pat. No. 6,102,850, which is a continuation-in-part of application Ser. No. 08/755,063, filed Nov. 22, 1996, now U.S. Pat. No. 5,855,583.

BACKGROUND OF THE INVENTION

1. Field of the Invention

The present invention generally relates to surgical devices. More particularly, the present invention relates to a device for suturing during the performance of minimally invasive endoscopic surgical procedures and more particularly to an articulating device for use in endoscopic coronary artery by-pass grafting surgery.

2. Description of Related Art

Blockage of a coronary artery may deprive the heart of the blood and oxygen required to sustain life. The blockage may be removed with medication or by an angioplasty. For severe blockage, a coronary artery bypass graft (CABG) is performed to bypass the blocked area of the artery. CABG procedures are typically performed by splitting the sternum and pulling open the chest cavity to provide access to the heart. An incision may be made in the artery adjacent to the blocked area. The internal mammary artery (IMA) or some other arterial source of blood-flow may then be severed and attached to the artery at the point of incision. The IMA bypasses the blocked area of the artery to again provide a full flow of blood to the heart.

Splitting the sternum and opening the chest cavity can create tremendous trauma on the patient. Additionally, the cracked sternum prolongs the recovery period of the patient. As such, there have been developed systems that enable minimally invasive CABG procedures. These systems utilize hand held tools and small incisions, on the order of 3–5 inches in length, to provide access to the thoracic region of a patient.

Such minimally invasive procedures are conducted by inserting surgical instruments through small incisions, on the order of inches in the skin of the patient. Manipulating such instruments can be awkward, particularly when suturing a graft to an artery. These systems utilize direct visualization of the surgical site. Such systems do not enable a completely endoscopic approach to the CABG procedure because of the need for direct visualization of the site. Additionally, such systems do not enable a fully endoscopic approach because of the incision size necessary to adequately manipulate the surgical instruments at the surgical site.

A fully endoscopic approach utilizes small holes to provide access to the thoracic cavity. Each of these holes is on the order of 3–11 mm in diameter. In order to perform a CABG procedure in a fully endoscopic fashion (i.e. using 3–11 mm holes) a robotic system must be used to filter hand tremors and scale motions made by the surgeon.

To facilitate the performance of an endoscopic surgical procedure, it would be useful to employ surgical instruments that can maneuver to the surgical site as well as manipulate tissue or sutures to perform an anastomosis.

To help minimize risk to the patient, and to minimize operating time, what is needed in the art is a robotically actuated surgical device that can articulate as well as actuate without being overly complex in design.

SUMMARY OF THE INVENTION

The present invention is an articulating device for tissue and needle manipulation, the device comprising:

An elongated housing having a proximal end and a distal end;

an articulation rod extending interior the housing, the articulation rod having a proximal end and a distal end;

an actuation rod extending interior the housing, the actuation rod having a proximal end and a distal end;

a rack driver in communication with the actuation rod at the distal end thereof, the rack driver engaged with a cylindrical rack for translating the motion of the actuation rod substantially about ninety degrees; and a jaw in communication with the cylindrical rack, whereby movement of the cylindrical rack actuates the jaw, the jaw further in pivotal communication with the articulation rod such that linear movement of the articulation rod produces rotational movement of the jaw.

BRIEF DESCRIPTION OF THE DRAWINGS

FIG. 3 is a cross-sectional perspective view of a device in accordance with the present invention in an opened straight configuration;

DETAILED DESCRIPTION OF THE INVENTION

Figure 1:
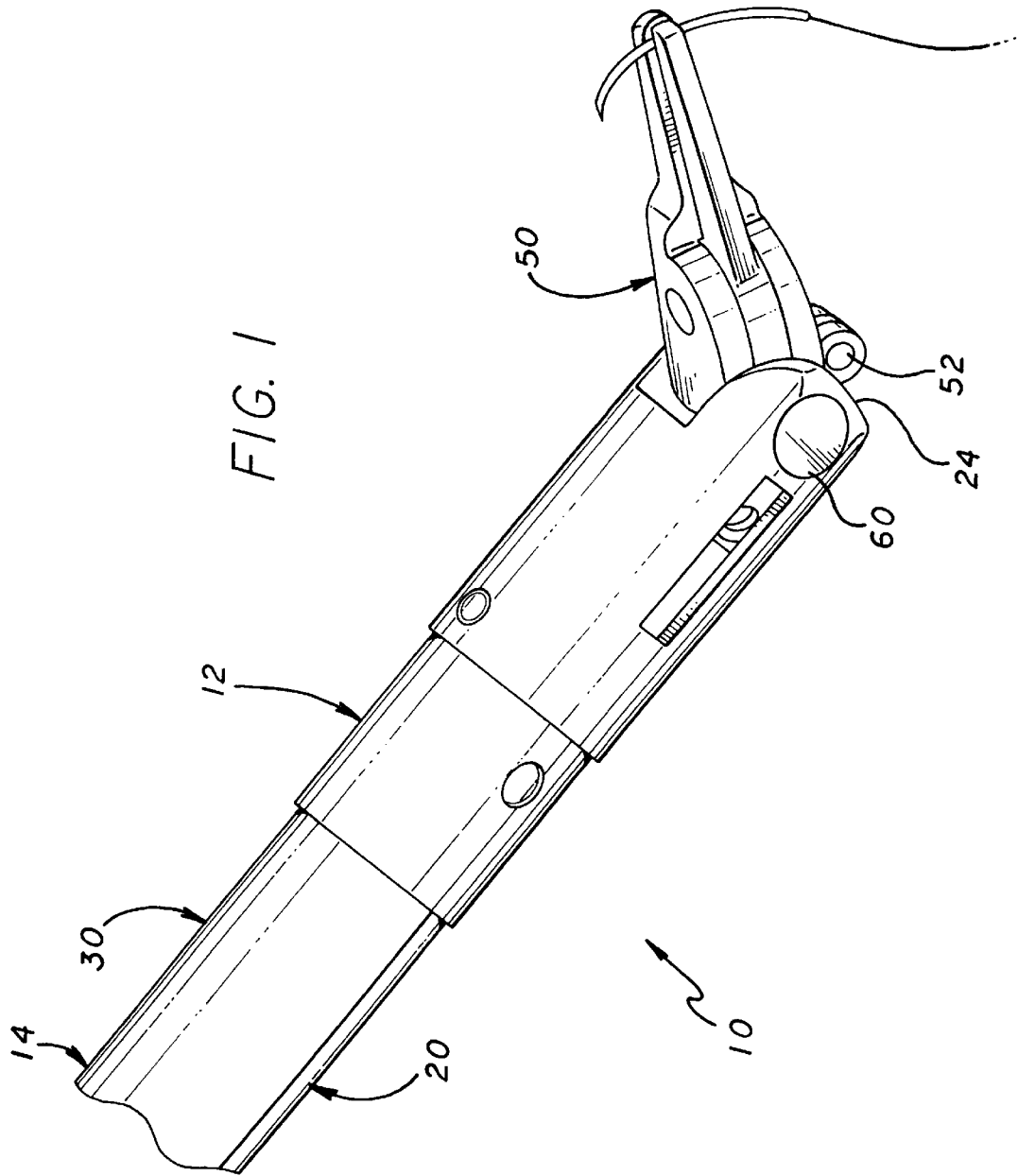
FIG. 1 is a partial break-away perspective view of a device in accordance with the present invention in a closed angled configuration.
Figure 2:
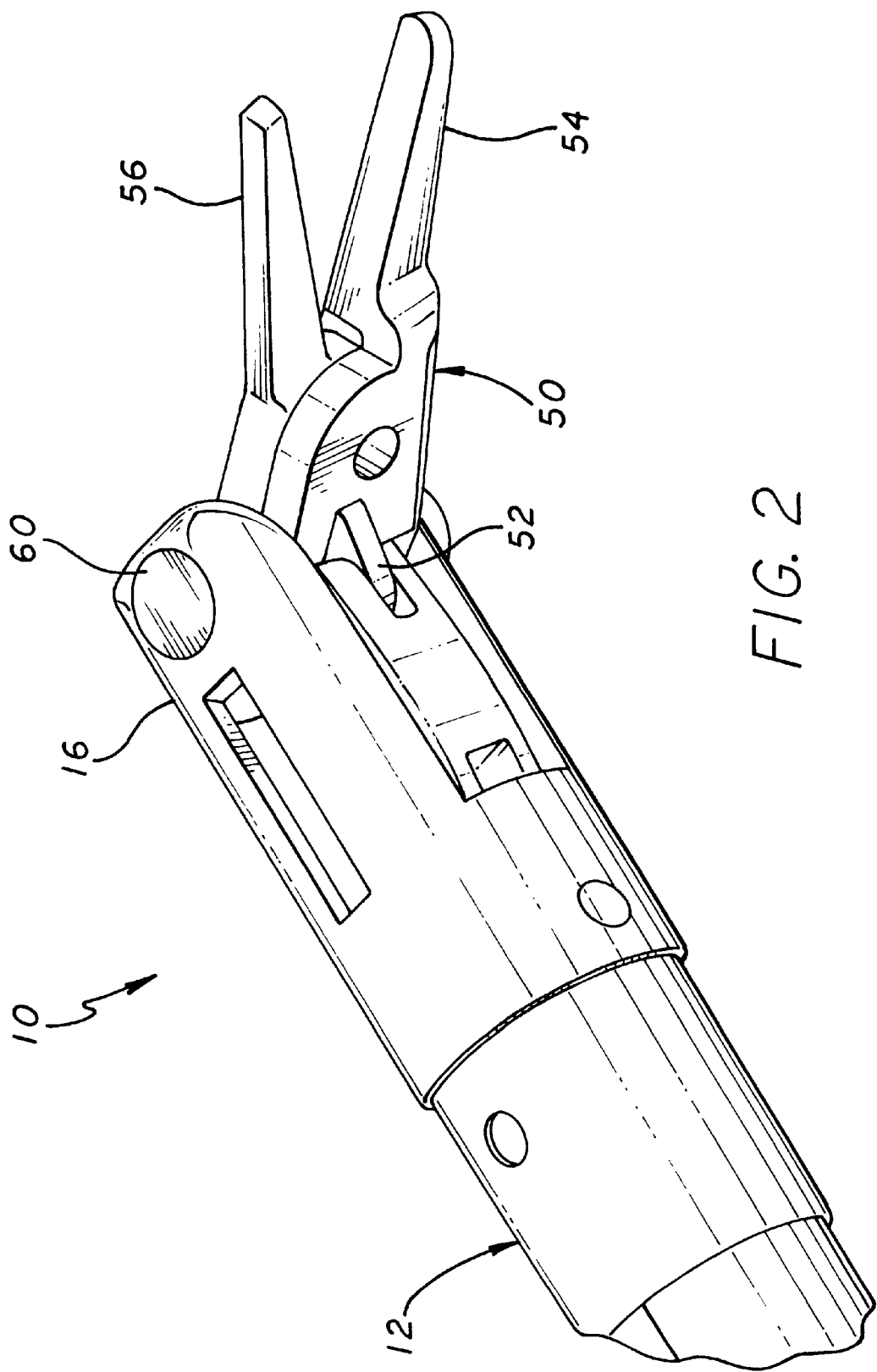
FIG. 2 is a partial break-away perspective view of a device in accordance with the present invention in an open angled configuration.

Referring to the drawings more particularly by reference numbers, FIGS. 1, 2 and 3 show a preferred embodiment of the articulating actuating device 10. The device 10 includes a housing 12. The housing extends substantially the length of the instrument 10 and has a proximal end 14 and a distal end 16 and a longitudinal axis X. Disposed interiorly the housing 12 is an articulation rod 20 and an actuation rod 30. Each of the articulation rod 20 and the actuation rod 30 have respective proximal ends 22, 32 and distal ends 24, 34.

The proximal ends 22, 32 of the rods may be attached to a robotic system for the performance of minimally invasive surgical procedures. One such system is produced by Computer Motion, Inc. The assignee hereof and is described in U.S. Pat. No. 5,855,583, which is incorporated herein by reference.

The rods 20, 30 are attached to actuators via attachment means taught in U.S. Pat. No. 5,855,583. Other means for removably attaching a rod to an actuator are known in the art including the use of screws, clips or the like. In this way, each of the rods 20, 30 may be driven by the actuator which is connected to various user interfaces and power sources and are conducive to the performance of minimally invasive surgical procedures.

The articulation rod 20 extends substantially the length of the housing 12 along its longitudinal axis X. The articulation rod 20 is pivotally connected to a jaw 50. Such a pivotal connection may be accomplished through the use of a hinge 52 attached intermediate the articulation rod 20 and the jaw 50.

The jaw 50 pivotally communicates with the housing 12 at the distal end 16 thereof through the use of a rack 60. In this way, motion of the articulation rod 20 results in rotation of the jaw 50. The rack 60 provides a pivot about which the jaw 50 rotates.

The actuation rod 30 provides for actuation of the jaw 50. The actuation rod has a pin 36 disposed at the distal end 34 thereof. The pin 36 seats in a rack channel 72 disposed in a rack driver 70. The rack driver is pivotally attached to the housing 12 via a pin 74 or the like. The housing has two longitudinal apertures 18, 19 formed therethrough at the distal end 16 thereof to provide for lateral movement of the rack driver 70 which shall be described in detail hereinbelow.

Longitudinal motion of the actuation rod 30 moves the pin 36 in the rack channel 72 which translates the longitudinal motion of the actuation rod 30 into a pivotal motion of the rack driver 70. The rack driver 70 pivots about the pivot point defined by the pin 74 which attaches the rack driver 70 to the housing 12. The rack driver 70 may move outside of the space defined as the interior of the housing through the longitudinal apertures 18, 19.

The rack driver 70 has a shoulder 76 which engages the rack 60. As the rack driver 70 pivots, the shoulder 76 causes the rack 60 to move laterally, which is orthogonal to the longitudinal motion of the actuation rod 30 and orthogonal to the longitudinal axis of the housing 12. The rack 60 is slidably moveable within the housing 12 through two cylindrical apertures 13, 15 formed therethrough. As the rack 60 moves laterally, the jaw 50 is actuated. The lateral movement of the rack 60 is transferred to a first jaw element 54. A second jaw element 56 is pivotally connected to the first jaw element 54 via a pin 58 or the like and is held stationary with respect to the first jaw element 54. In this way, as the first jaw element is 54 is moved, the second jaw element 56 remains stationary and the jaw 50 is actuated. If each element has a sharp edge, then the jaw may function as a scissors.

The jaw 50 is always in communication with the rack 60, even as it is articulated through the motion of the articulation rod 20. This is accomplished through the use of a cylindrical rack having a circumferential channel 66 formed therein. The channel 66 receives the shoulder 76 of the rack driver 70 as well as a shoulder 58 on the first jaw element 54. As such, as the jaw 50 is articulated, the shoulder 58 on the first jaw element 54 rotates within the circumferential channel 66 in the rack 60 maintaining communication therein and providing for actuation of the jaw 50 regardless of the articulated position of the jaw 50 caused through motion of the articulation rod 20.

In this fashion, the articulation of the jaw 50 and the actuation of the jaw 50 are decoupled. It is highly advantageous to provide for a rigidly linked device that is decoupled in this fashion for several reasons. First, the device is easily steralizable and secondly, the device is quite safe to use as there is no use of tensioned cables or the like.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. An articulating device for tissue and needle manipulation, the device comprising:

an elongated housing having a proximal end and a distal end;

an articulation rod extending interior the housing, the articulation rod having a proximal end and a distal end;

an actuation rod extending interior the housing, the actuation rod having a proximal end and a distal end;

a rack driver in communication with the actuation rod at the distal end thereof, the rack driver engaged with a cylindrical rack for translating the motion of the actuation rod substantially about ninety degrees; and a jaw in communication with the cylindrical rack, whereby movement of the cylindrical rack actuates the jaw, the jaw further in pivotal communication with the articulation rod such that linear movement of the articulation rod produces rotational movement of the jaw.

* * * * *